United States Patent [19]
Sanders et al.

[11] Patent Number: 6,039,738
[45] Date of Patent: *Mar. 21, 2000

[54] FASTENER

[75] Inventors: Marcus Maria Sanders, Cleveland Hts.; John Mark Kapitan, Shaker Hts.; Henry John Harding Brown, Solon, all of Ohio

[73] Assignee: Depuy Orthopaedics, Inc., Warsaw, Ind.

[ * ] Notice: This patent is subject to a terminal disclaimer.

[21] Appl. No.: 09/186,567

[22] Filed: Nov. 5, 1998

Related U.S. Application Data

[63] Continuation of application No. 08/887,832, Jul. 3, 1997, Pat. No. 5,899,902.

[51] Int. Cl.[7] .................................................. A61B 17/70
[52] U.S. Cl. ............................... 606/61; 606/73; 606/104
[58] Field of Search ............................... 606/61, 60, 72, 606/73; 623/17

[56] References Cited

U.S. PATENT DOCUMENTS

| | | |
|---|---|---|
| 4,269,246 | 5/1981 | Larson et al. . |
| 4,854,311 | 8/1989 | Steffee . |
| 5,019,079 | 5/1991 | Ross . |
| 5,024,213 | 6/1991 | Asher et al. . |
| 5,085,660 | 2/1992 | Lin . |
| 5,129,900 | 7/1992 | Asher et al. . |
| 5,257,994 | 11/1993 | Lin . |
| 5,290,288 | 3/1994 | Vignaud et al. . |
| 5,443,482 | 8/1995 | Stone et al. . |
| 5,487,744 | 1/1996 | Howland . |
| 5,571,184 | 11/1996 | DeSatnick . |
| 5,620,443 | 4/1997 | Gertzbein et al. . |
| 5,643,260 | 7/1997 | Doherty . |
| 5,653,708 | 8/1997 | Howland . |
| 5,653,710 | 8/1997 | Harle . |

FOREIGN PATENT DOCUMENTS

| | | |
|---|---|---|
| 0726 064 | 8/1996 | European Pat. Off. . |
| 93 21848 | 11/1993 | WIPO . |
| 96 02199 | 2/1996 | WIPO . |
| 96 02200 | 2/1996 | WIPO . |

*Primary Examiner*—Michael Buiz
*Assistant Examiner*—David O. Reip

[57] ABSTRACT

An improved fastener is provided for use in retaining vertebrae in a desired spatial relationship. The fastener has a mounting section with a first external thread to engage a vertebra. The fastener has a retaining section with a second external thread to engage an internal thread on a retaining element, such as a nut. A circular intermediate section interconnects the mounting and retaining sections of the fastener. A plurality of spaced apart recesses are formed in the intermediate section. Each of these recesses has a surface for receiving force to rotate the fastener relative to a vertebra. The circular intermediate section may include an annular end surface which faces toward a retaining section and a cylindrical outer side surface. Each of the recesses has an opening which extends from the annular end surface into the cylindrical side surface.

31 Claims, 3 Drawing Sheets

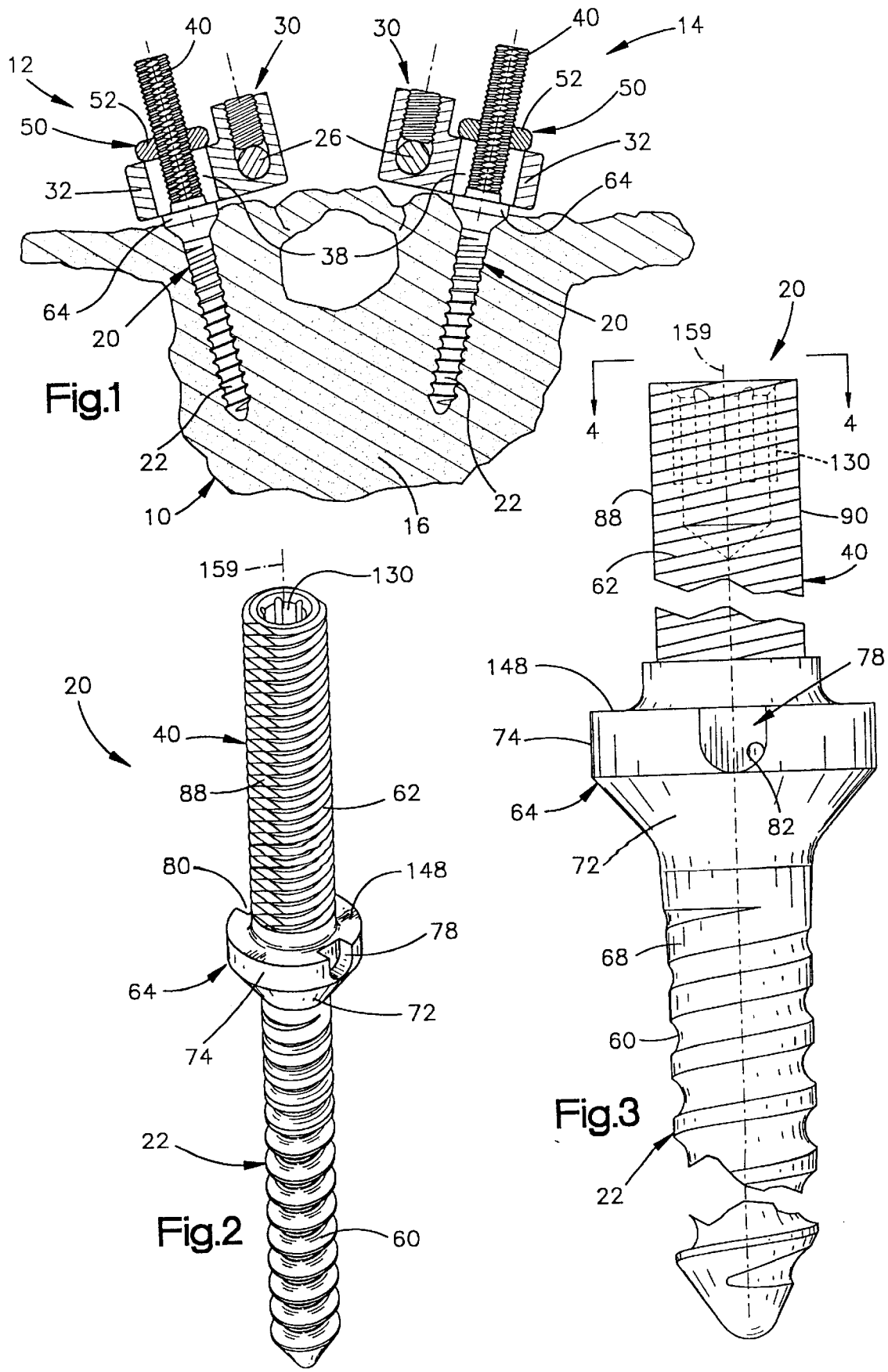

6,039,738

FASTENER

This application is a continuation of application Ser. No. 08/887,832, filed Jul. 3, 1997, now U.S. Pat. No. 5,899,902.

BACKGROUND OF THE INVENTION

The present invention relates to a new and improved fastener for use in retaining vertebrae in a desired spatial relationship.

Known fasteners have been used to retain vertebra in a desired spatial relationship. At least one of these known fasteners has a mounting section with an external thread convolution which engages bone in a vertebra. This known fastener has a retaining section which extends axially outward from the mounting section. An external thread convolution is provided on the retaining section for engagement with an internally threaded element, that is, a nut.

A hexagonal intermediate or head section is provided between the mounting and retaining sections of the known fastener. The intermediate or head section of the known fastener is engageable by a tool to rotate the known fastener relative to a vertebra. A fastener having this construction is disclosed in U.S. Pat. No. 4,854,311. Other known fasteners which are used to retain vertebrae in a desired spatial relationship are disclosed in U.S. Pat. Nos. 5,085,660; 5,257,994; and 5,620,443.

SUMMARY OF THE INVENTION

The present invention provides a new and improved fastener to retain vertebrae in a desired spatial relationship. The fastener includes a mounting section having an external thread convolution which engages a vertebra. The fastener has a retaining section with an external thread convolution to engage an internally threaded retainer member. An intermediate or head section is disposed between and is connected with the retaining and mounting sections. The intermediate section includes a plurality of spaced apart recesses having surfaces which receive force to rotate the fastener relative to a vertebra.

The intermediate or head section may have a circular configuration with an end surface which faces toward the retaining section and a side surface which faces outward from a central axis of the fastener. Each of the recesses in the intermediate section have an opening which extends from the end surface into the side surface of the intermediate section and through which a portion of a tool is movable.

BRIEF DESCRIPTION OF THE DRAWINGS

The foregoing and other features of the present invention will become more apparent upon a consideration of the following description taken in connection with the accompanying drawings, wherein:

FIG. 1 is a simplified schematic illustration depicting the manner in which a pair of fasteners constructed in accordance with the present invention are connected with a vertebra in a spinal column;

FIG. 2 is an enlarged pictorial illustration of one of the fasteners of FIG. 1;

FIG. 3 is an enlarged fragmentary view of the fastener of FIG. 2;

DESCRIPTION OF SPECIFIC PREFERRED EMBODIMENT OF THE INVENTION

General Description

Figure 4:
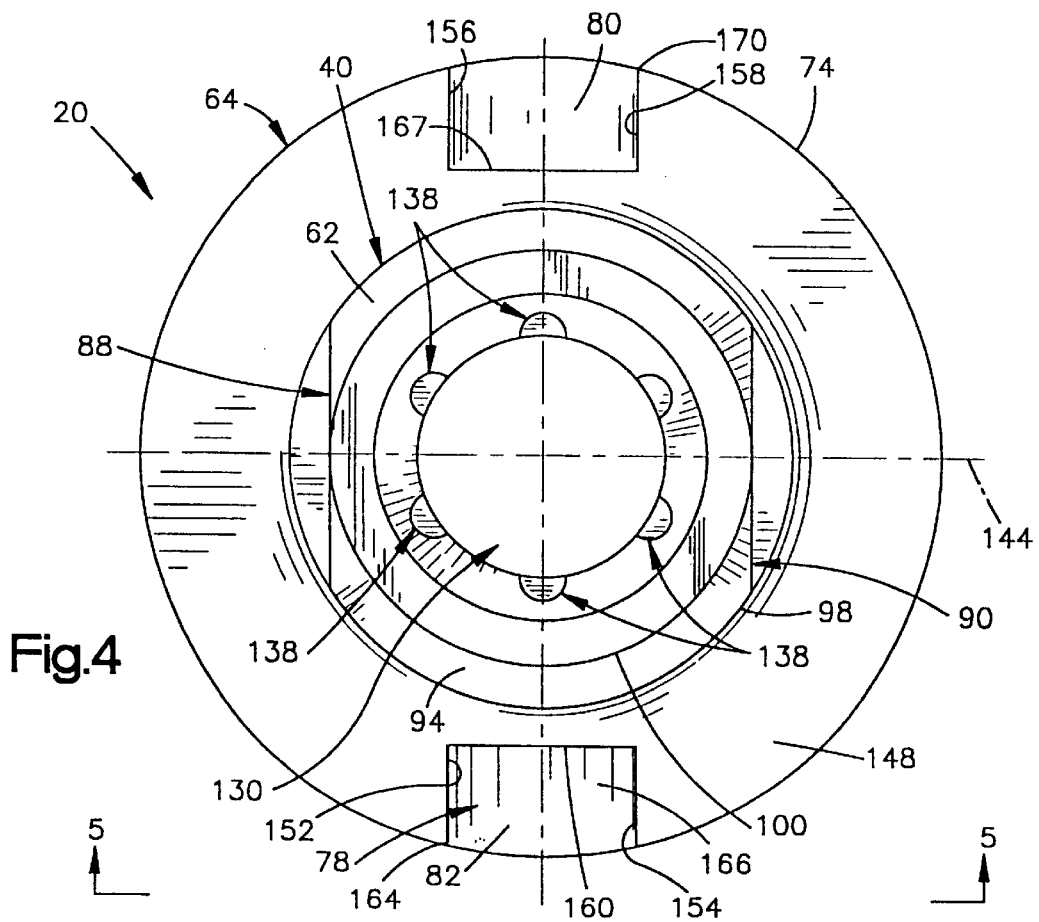
FIG. 4 is an end view, taken generally along the line 4—4 of FIG. 3, illustrating the construction of a retaining section and intermediate section of the fastener of FIG. 2.

A human spinal column 10 to which a pair of retainer assemblies 12 and 14 are connected is illustrated in FIG. 1. The retainer assemblies 12 and 14 retain portions of the spinal column, that is vertebrae 16, in a desired spatial relationship relative to each other.

The retainer assemblies 12 and 14 have the same construction and include fasteners 20 constructed in accordance with the present invention. In the illustrated embodiment of the invention, the fasteners are formed of one piece of biocompatible material, specifically, anodized titanium. However, the fasteners 20 could be formed of a different material if desired. For example, the fasteners 20 could be formed of stainless steel.

The fasteners 20 have inner end or mounting sections 22 which engage bone in the vertebra 16 to fixedly mount the fasteners in the vertebra. Although only a pair of fasteners 20 have been shown in FIG. 1, it should be understood that there are additional fasteners 20 connected with adjacent vertebrae 16 of the spinal column 10.

Each of the retainer assemblies 12 and 14 (FIG. 1) includes a longitudinal member, such as a cylindrical rod 26, which extends along the spinal column 10. The rods 26 are made of a biocompatible material, such as stainless steel or titanium. Each of the rods 26 has a length which is sufficient to enable the rod to span at least two of the vertebrae 16 in the spinal column 10. Of course, the length of the rods 26 in any particular installation will depend upon the condition to be corrected and the number of vertebrae 16 to be held in a desired spatial relationship relative to each other by the retainer assemblies 12 and 14. The rods 26 may be bent to conform to a desired curvature of the spinal column 10 in all or any of the three possible anatomic planes.

Connector assemblies 30 interconnect the rods 26 and the fasteners 20. Each of the connector assemblies 30 includes a retainer member 32. Each of the retainer members 32 is provided with an opening through which one of the rods 26 extends. Each of the retainer members 32 has a second opening or slot 38 through which a retaining section 40 of a fastener 20 extends.

Retaining clamps 50 hold the retainer members 32 against movement relative to the fasteners 20. The retaining clamps 50 include internally threaded retainer nuts 52 which engage threads on the retaining sections 40 of the fasteners 20. Locknuts may be provided to clamp the retainer nuts 52 in place on the fasteners 20.

The distance between the rods 26 and the fasteners 20 can be varied while the rods 26 and fasteners are connected with the retainer members 32 and while the fasteners 20 remain stationary relative to the vertebrae 16. To enable temporary relative movement to occur between the rods 26 and fasteners 20, the slots 38 in the connector members 32 have an oblong configuration. Therefore, a vertebra 16 engaged by a fastener 20 can be moved either toward or away from a rod 26 which is being held substantially stationary.

The general construction of the retainer assemblies 12 is similar to the construction of retainer assemblies disclosed in U.S. Pat. No. 5,129,900. However, it should be understood that the retainer assemblies 12 and 14 could have any desired construction. For example, the retainer assemblies 12 and 14 could be constructed in the manner disclosed in U.S. Pat. Nos. 4,854,311 or 5,024,213 if desired.

The fastener 20, which is constructed in accordance with the present invention, has a mounting section 22 with a helical external thread convolution 60 (FIGS. 2 and 3) which engages one of the vertebrae 16 (FIG. 1). The thread convolution 60 engages the bone in vertebra 16. The retaining section 40 (FIGS. 2 and 3) has a helical external thread convolution 62 which engages one of the retainer nuts 52.

A circular intermediate or head section 64 is disposed between the mounting section 22 and retaining section 40. The intermediate section 64 projects radially outward of the mounting section 22 and retaining section 40. The external thread convolutions 60 and 62, mounting section 22, retaining section 40, and intermediate section 64 all have central axes which are coincident with a central axis of the fastener 20.

Fastener—Mounting and Intermediate Sections

The mounting section 22 of the fastener 20 has the external thread convolution 60 to connect the fastener with a vertebra. The external thread convolution 60 is a coarse helical thread convolution. A six (6) degree taper or runout is provided at an upper (as viewed in FIG. 3) end portion 68 of the external thread convolution 60. The external thread convolution 60 may have a configuration similar to the configuration disclosed in U.S. Pat. No. 4,854,311. However, it should be understood that the external thread convolution 60 could have any desired configuration. It is believed that a relatively coarse thread convolution will probably be preferred in order to provide secure engagement with bone in a vertebra 16.

The intermediate or head section 64 (FIG. 3) is disposed in a coaxial relationship with the mounting section 22 and retaining section 40. The intermediate section 64 has a generally circular cross sectional configuration. The intermediate section 64 includes a lower side or end surface 72 which forms a portion of a cone.

The conical side or end surface 72 has a central axis which is coincident with the central axis of the fastener 20. The side surface 72 flares radially outward and axially upward (as viewed in FIG. 3) from the outer end portion 68 of the mounting section 22 toward the retaining section 40. It is contemplated that the side surface 72 may be pressed against a vertebra 16 when the fastener 20 is used to retain the vertebrae in a desired spatial relationship. The intermediate or head section 64 also includes a cylindrical side surface 74 which is disposed in a coaxial relationship with the conical side surface 72 and the mounting section 22.

In accordance with a feature of the present invention, a pair of identical recesses 78 and 80 (FIG. 2) are formed in portions of the intermediate section 64. The recesses 78 and 80 are diametrically opposite from each other. The recesses 78 and 80 have generally rectangular (FIG. 4) open end portions which face upward (as viewed in FIG. 2) toward the retaining section 40. The recess 78 (FIG. 3) has an arcuate bottom surface 82 with a center of curvature disposed on a radius of the cylindrical side surface 74. The recesses 78 and 80 are engageable by a suitable tool to rotate the mounting section 22 relative to a vertebra 16.

Fastener—Retaining Section

The retaining section 40 (FIGS. 2 and 3) of the fastener 20 is formed as one piece with and is disposed in a coaxial relationship with the mounting section 22 and intermediate section 64. The external thread convolution 62 on the retaining section 40 is disposed in a coaxial relationship with the external thread convolution 60 on the mounting section 22. A retainer nut 52 (FIG. 1) engages the external thread convolution 62 on the retaining section 40 to hold the retainer member 32 against movement relative to the fastener 20.

Parallel flats 88 and 90 (FIG. 4) are formed on opposite sides of the retaining section 40. The parallel flats 88 and 90 extend between axially opposite ends of the retaining section 40 (FIG. 2). The identical flats 88 and 90 engage parallel sides of the slot 38 (FIG. 1) in the retainer member 32 to block relative rotation between the fastener 20 and the retainer member 32.

The slot 38 in the retainer member 32 is sized so as to accommodate sliding adjustment between the retainer member 32 and fastener 20. Of course, when the retainer nut 52 is tightened, the retainer member 32 is securely clamped between the intermediate section 64 and the retainer nut to hold the retainer member against movement relative to the fastener 20.

Figure 6:
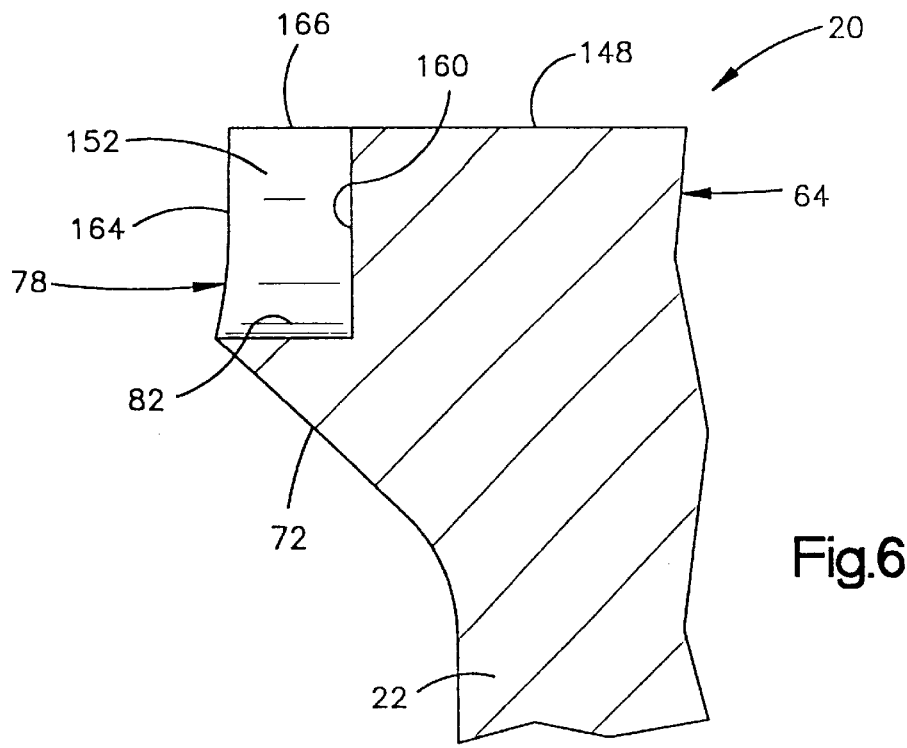
FIG. 6 is a fragmentary sectional view, taken generally along the line 6—6 of FIG. 5, further illustrating the construction of a recess in the intermediate or head section of the fastener.

The flats 88 and 90 (FIG. 4) are separated by a distance which is substantially equal to or greater than a root diameter of the external thread convolution 62. The external thread convolution 62 has helical flank surfaces 94 and 96 (FIG. 6) which intersect at a helical crest 98 and a helical root 100 on the external thread convolution 62. The external thread convolution 62 is formed in a cylindrical shank portion 104 of the retaining section 40.

In the illustrated embodiment of the retaining section 40, the distance between the flats 88 and 90 (FIG. 4) is equal to the root diameter of the external thread convolution 62. This results in the parallel flats 88 and 90 extending tangentially to the root 100 of the external thread convolution 62. Therefore, the minimum distance between the flats 88 and 90, that is, the distance as measured along a diametral axis perpendicular to the flats, is equal to the diameter of the root 100 of the external thread convolution 62.

By having the distance between the flats 88 and 90 (FIG. 4) equal to the root diameter of the external thread convolution 62, the shank portion 104 of the retaining section 90 is not weakened by removal of material to form the flats 88 and 90. In order to form the flats 88 and 90, only the material of the external thread convolution 62 is removed from the retaining section 40. This results in the strength of the shank portion 104 being substantially the same before and after the flats 88 and 90 are formed on the retaining section 40.

A drive recess 130 (FIGS. 2, 3 and 4) is formed in the outer or upper end portion of the retaining section 40. The drive recess 130 receives a drive tool (not shown). Force is applied to the drive tool to rotate the fastener 20 relative to the vertebra 16.

The drive recess 130 includes a cylindrical main portion 134 and a plurality of arcuate corner portions 138 (FIG. 4). The corner portions 138 receive projecting portions of the drive tool. Force is transmitted from the drive tool to the corner portions 138 of the recess 130 to rotate the fastener 20 relative to a vertebra 16. The corner portions 138 are offset from a plane which contains the center line of the fastener 20 and extends perpendicular to the flats 88 and 90. The plane which contains the center line of the fastener 20 and extends perpendicular to the flats 88 and 90 is a diametral plane of the fastener and has been indicated at 144 in FIG. 4.

By having the corner portions 138 offset from the diametral plane 144, the corner portions are disposed in a portion of the shank where the external thread convolution 62 has not been interrupted to form the flats 88 and 90. This tends to maximize the strength of the shank portion 104 at the locations where the corner portions 138 are formed. Therefore, the corner portions 138 are capable of transmitting relatively large driving forces (torque) without fracturing of the material of the shank portion 104 adjacent to the corner portions 138.

Fastener—Intermediate Section

The intermediate or head section 64 of the fastener 20 has a circular cross-sectional configuration. A lower (as viewed in FIG. 5) portion of the intermediate section 64 is formed by the conical end surface 72. A cylindrical side surface 74 extends upward from the conical end surface 72. A flat annular upper end surface 148 extends radially inward from the cylindrical side surface 74. The upper end surface 148 is disposed in a plane which extends perpendicular to a central axis of the fastener 20. The upper end surface 148 is disposed in a coaxial relationship with the conical end surface 72 and the cylindrical side surface 74.

Figure 7:
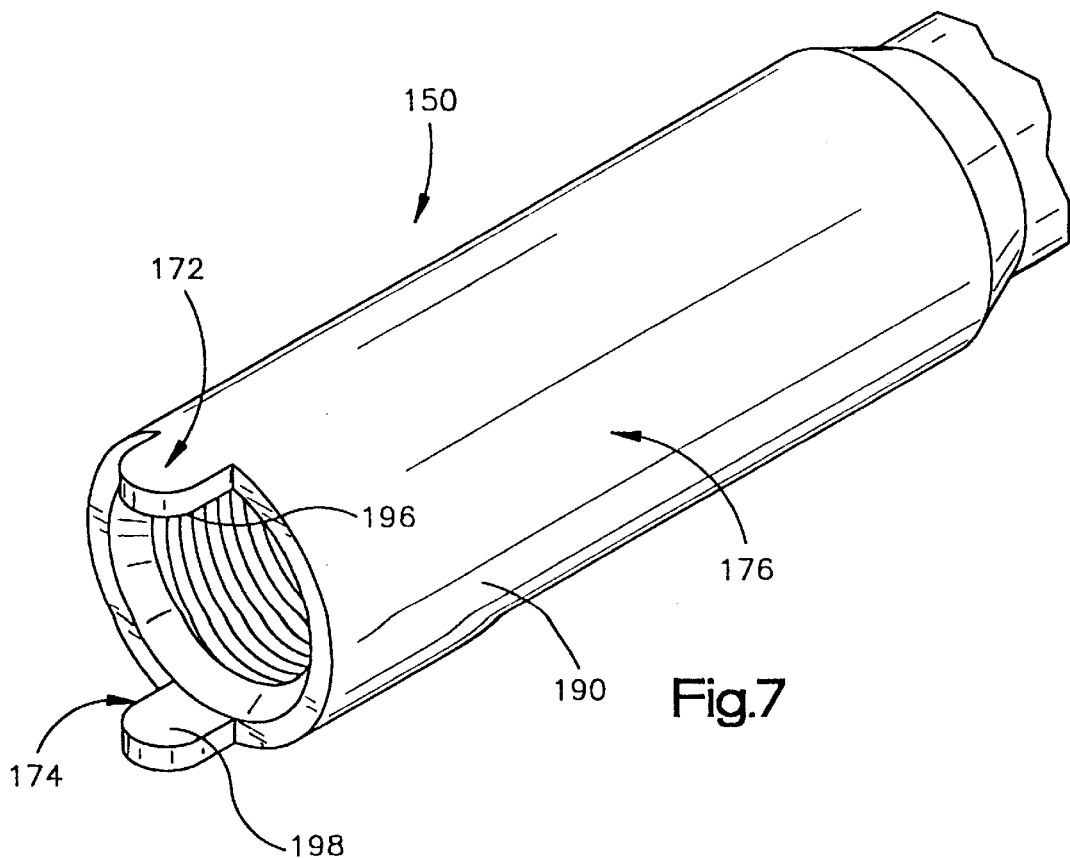
FIG. 7 is a fragmentary pictorial illustration of a tool which applies force to surfaces of the recesses in the intermediate or head section of the fastener of FIGS. 1–6.

In order to facilitate removal and/or driving of the fastener 20, the recesses 78 and 80 are formed in the intermediate sections 64 of the fastener. The identical recesses 78 and 80 are simultaneously engageable by a tool 150 (FIG. 7) to apply force against surfaces of the recesses 78 and 80 to rotate the fastener relative to the vertebra 16. It is contemplated that the provision of the recesses 78 and 80 will be particularly advantageous in the very unlikely event that the retaining section 40 breaks loose from the mounting section 22 for any reason.

Figure 5:
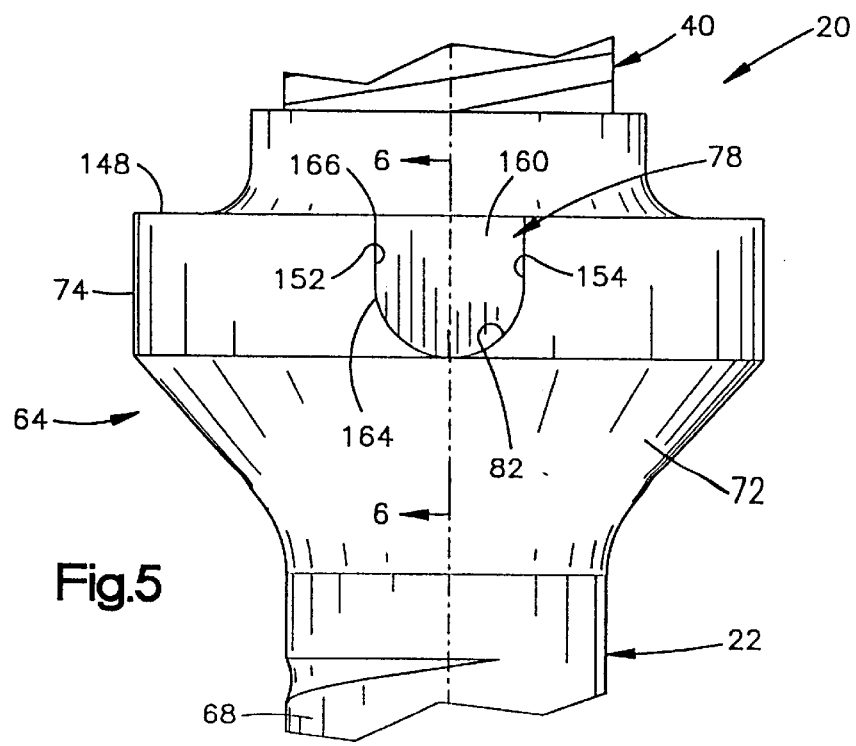
FIG. 5 is an enlarged fragmentary view, taken along the line 5—5 of FIG. 4, further illustrating the construction of the intermediate or head section of the fastener of FIG. 3.

In addition to the semi-circular bottom surface 82, the recess 78 includes a pair of flat parallel side surfaces 152 and 154 (FIG. 5). The side surfaces 152 and 154 extend perpendicular to the flat annular, radially extending upper end surface 148 of the intermediate section 64. The recess 80 (FIG. 4) has side surfaces 156 and 158 (FIG. 4) which are disposed in the same parallel planes as the side surfaces 152 and 154 of the recess 78.

The semi-circular bottom surface 82 of the recess 78 (FIG. 5) has a center of curvature which is disposed on a radius of the cylindrical side surface 74. Thus, the center of curvature of the bottom surface 82 is disposed on an axis which extends perpendicular to and intersects the longitudinal central axis 159 (FIG. 3) of the fastener 20. The bottom surface 82 (FIGS. 5 and 6) has the same arc of curvature throughout the extent of the bottom surface.

The arcuate bottom surface 82 of the recess 78 extends radially inward from the cylindrical side surface 74 (FIGS. 4 and 5) to a location disposed approximately midway between the external thread convolution 62 on the retaining section 40 (FIG. 4) and the cylindrical side surface 74. The recess 78 has an end wall 160 which extends perpendicular to the side surfaces 152 and 154. The end wall 160 has the same configuration as an opening 164 in the cylindrical side surface 74 (FIG. 5). The end wall 160 extends parallel to the central axis 159 (FIG. 3) of the fastener 20. In addition to the opening 164 in the cylindrical side surface 74, the recess 78 has a generally rectangular opening 166 (FIG. 4) in the flat annular end surface 148 of the intermediate section 64.

The recess 80 has the same configuration as the recess 78. The recess 80 has an end wall 167 (FIG. 4) which extends parallel to the end wall 160 of the recess 78. The recess 80 has a semi-circular bottom surface 168 which has a central axis which is coincident with the central axis of the bottom surface 82 of the recess 78. The recess 80 has an opening 170 which extends from the end surface 148 into the cylindrical side surface 74.

In the illustrated embodiment of the invention, there are only two recesses 78 and 80 in the intermediate section 64. However, it should be understood that a greater number of recesses could be provided if desired. In the illustrated embodiment of the invention, the recess 78 extends radially inward from the cylindrical side surface 78 of the intermediate section 64. However, the recess 78 could, if desired, extend into the portion of the intermediate section enclosed by the conical end surface 72. The recess 80 has the same configuration and relationship to the intermediate section 64 as the recess 78.

Fastener Rotation Tool

The tool 150 (FIG. 7) has a pair of projections 172 and 174 which are movable through the openings 166 and 170 (FIG. 4) into the recesses 78 and 80. The projections 172 and 174 then apply force against side surfaces of the recesses 78 and 80. The tool 150 (FIG. 7) includes a cylindrical body or main portion 176. The projections 172 and 174 are formed at the lower (as viewed in FIG. 7) end of the cylindrical body portion 176.

The projections 172 and 174 have the same configuration as the recesses 78 and 80. Thus, the projections 172 and 174 are shaped for mating engagement with the recesses 78 and 80. The body portion 176 has an outer side surface 190 which forms a portion of a cylinder having the same diameter as the cylindrical side surface 74 of the intermediate section 64. In the illustrated embodiment of the invention, the projections 172 and 174 have inner side surfaces 196 and 198 which form a portion of a cylinder having an axis which is coincident with the axis of the cylindrical outer side surface 190 of the tool 150. The inner side surfaces 196 and 198 on the projections 172 and 174 are spaced apart by a distance which is greater than the distance between the end surfaces 160 and 168 of the recesses 78 and 80. Therefore, the projections 172 and 174 do not completely fill the recesses 78 and 80. However, the projections 172 and 174 could be configured so as to completely fill the recesses 78 and 80 if desired.

When the fastener 20 is to be rotated relative to a vertebra 16 by the tool 150, the tool is moved axially downward (as viewed in FIG. 7) until the projections 172 and 174 enter the recesses 78 and 80 (FIG. 4) through the openings 166 and 170 in the intermediate section 64 of the fastener 20. Force (torque) is then applied to the tool 150. This force is transmitted through the body 176 of the tool 150 to the projections 172 and 174.

Side surfaces and arcuate end surfaces on the projections 172 and 174 press against side surfaces on the recesses 78 and 80 to rotate the fastener in either a clockwise or a counterclockwise direction relative to the vertebra. When the fastener 20 is to be installed in the vertebra 16, the tool 150 may be utilized to rotate the fastener in a clockwise direction and thereby increase the force with which the intermediate section 64 is pressed against the vertebra. Alternatively, the tool 150 may be rotated in a counterclockwise direction to rotate the fastener to disengage the fastener from the vertebra.

Conclusion

The present invention provides a new and improved fastener 20 to retain vertebrae 16 in a desired spatial relationship. The fastener 20 includes a mounting section 22 having an external thread convolution 60 which engages a vertebra 16. The fastener 20 has a retaining section 40 with an external thread convolution 62 to engage an internally threaded retainer member 52. An intermediate or head section 64 is disposed between and is connected with the retaining and mounting sections 22 and 40. The intermediate section 64 includes a plurality of spaced apart recesses 78 and 80 having surfaces which receive force to rotate the fastener 20 relative to a vertebra 16.

The intermediate or head section 64 may have a circular configuration with an end surface 148 which faces toward the retaining section and a side surface 74 which faces outward from a central axis 159 of the fastener. Each of the recesses 78 and 80 in the intermediate section 64 have an opening 164 which extends from the end surface 148 into the side surface 74 of the intermediate section 64 and through which a portion of a tool is movable.

What is claimed is:

1. A fastener for use in retaining vertebrae in a desired spatial relationship, said fastener comprising
   a mount section having threads adapted to engage a vertebra,
   a head extending radially outwardly from the mount, the head including an end surface facing away from the mount section, a side surface disposed in a generally coaxial relationship with the threads, and spaced-apart first and second recesses each having an opening that is at least partially defined by the side surface, the first and second recesses being separated by a continuous segment of the end surface that is generally free of discontinuities, and
   a retainer coupled to the head and including second external threads adapted to engage an internally threaded member.

2. The fastener of claim 1, wherein the retainer is in a generally coaxial relationship with the mount section.

3. The fastener of claim 2, wherein the retainer includes retaining sections formed to include the threads and opposite generally parallel flats.

4. The fastener of claim 2, wherein the retainer includes an end portion opposite the head and the end portion includes a recess therein.

5. The fastener of claim 2, wherein the retainer includes opposite sides and the first recess is positioned adjacent to the first side and the second recess is positioned adjacent to the second side.

6. The fastener of claim 1, wherein the end surface is generally circular in shape.

7. The fastener of claim 6, wherein the side surface is generally cylindrical in shape.

8. The fastener of claim 6, wherein the recesses each have an opening that is at least partially defined by the side surface.

9. The fastener of claim 1, wherein each recess includes an open end portion that faces away from the mount section.

10. The fastener of claim 9, wherein a central axis extends through the mount section and each recess includes an open portion that faces radially outward from the central axis.

11. A fastener for use in retaining vertebrae in a desired spatial relationship, said fastener comprising
    a mount section having threads adapted to engage a vertebra,
    a head extending radially outwardly from the mount, the head including an end surface facing away from the mount section, a side surface disposed in a generally coaxial relationship with the threads, and spaced-apart first and second recesses each having an opening that is at least partially defined by the side surface, the first and second recesses being separated by a continuous segment of generally free of discontinuities, and
    a retainer coupled to the head and including second external threads adapted to engage an internally threaded member, and the retainer includes an end portion opposite the head and the end portion includes a recess therein, and the recess in the end portion is defined by corner portions.

12. A fastener for use in retaining vertebrae in a desired spatial relationship, the fastener comprising:
    a mount section including threads adapted to engage a vertebra, the threads having a thread convolution with a flank surface adapted to engage bone in the vertebra to hold the thread convolution against axial movement relative to the vertebra,
    a head coupled to the mount section and projecting radially outward of the thread convolution, the head including an end surface, a side surface having opposite first and second portions, a first recess disposed adjacent to the first portion of the side surface, and a second recess disposed adjacent to the second portion of the side surface, the first and second recesses being separated by opposing continuous segments of the end surface, the continuous segments each having opposite ends and being substantially free of discontinuities, the first and second recesses extending from the opposite ends of the continuous segments in a direction toward the mount section and being at least partially disposed radially outward of the thread convolution on the mount section; and
    a retainer coupled to the head extending axially outward from the end surface of the head.

13. The fastener of claim 12, wherein the end surface of the head faces away from the mount section and a side surface disposed in a generally coaxial relationship with the thread convolutions.

14. The fastener of claim 13, wherein the recesses each have an opening that is at least partially defined by the end surface.

15. The fastener of claim 13, wherein the recesses each have an opening that is at least partially defined by the side surface.

16. The fastener of claim 15, wherein the opening of each of the recesses is at least partially defined by the end surface.

17. The fastener of claim 12, wherein the first and second recesses each include an opening that faces away from the thread convolution.

18. The fastener of claim 12, wherein the retainer includes threads.

19. An apparatus comprising:
    a fastener including amount section, including threads adapted to engage a vertebra, the threads having a thread convolution with a flank surface adapted to engage bone in the vertebra to hold the thread convolution against axial movement relative to the vertebra,
    a head coupled to the mount section and projecting radially outward of the thread convolution, the head including a first recess and a second recess spaced-apart from the first recess, the first and second recesses each including an opening having a first portion facing outward of the head away from a central axis of the fastener and a second portion facing in a direction along the central axis,
    a tool including a first portion being moveable through the first and second portions of the first opening and a second portion being moveable through the first and second portions of the second opening, the first and second portions being configured to apply a force against the head to rotate the fastener, and
    a retainer coupled to the head extending away from the head along the central access.

20. The apparatus of claim 19, wherein the retainer includes second external threads adapted to engage an internally threaded member.

21. The fastener of claim 20, wherein the head is coupled between the mount and the retainer.

22. The fastener of claim 20, wherein the retainer includes opposite sides and the first recess is positioned adjacent to the first side and the second recess is positioned adjacent to the second side.

23. An apparatus comprising a fastener including a mount section including threads adapted to engage a vertebra, the threads having a thread convolution with a flank surface adapted to engage bone in the vertebra to hold the thread convolution against axial movement relative to the vertebra, a head coupled to the mount section and projecting radially outward of the thread convolution, the head including a first recess and a second recess spaced-apart from the first recess, the first and second recesses each including an opening having a first portion facing outward of the head away from a central axis of the fastener and a second portion facing in a direction along the central axis, and a retainer coupled to the head and including second external threads adapted to engage an internally threaded member, a tool including a first portion being movable through the first and second portions of the first opening and a second portion being movable through the first and second portions of the second opening, the first and second portions being configured to apply a force against the head to rotate the fastener, a retainer coupled to the head and including second external threads adapted to engage an internally threaded member, and the retainer includes an end portion opposite the head and the end portion includes a recess therein.

24. The fastener of claim 23, wherein the recess in the end portion is defined by corner portions.

25. A fastener for use in retaining vertebrae in a desired spatial relationship, the fastener comprising:

a mounting section having thread means for engaging a vertebra, said thread means including an external thread convolution having flank surface means for engaging bone in the vertebra to hold said external thread convolution against axial movement relative to the vertebra, a head section which is connected to said mounting section and projects radially outward of said external thread convolution, said head section including a circular end surface and a circular side surface, a first recess disposed in said head section through a first portion of said circular side surface of said head section, and a second recess formed separately from said first recess and disposed in said head section through a second portion of said circular side surface of said head section which is positioned to lie opposite the first portion, said first and second recesses being separated by a continuous segment of said circular end surface, said continuous segment of said circular end surface being formed as a portion of a circle being free of discontinuities, said first and second recesses extend from opposite ends of said continuous segment of said circular end surface in a direction toward said mounting section and are at least partially disposed radially outward of said external thread convolution on said mounting section; and a retaining section which is connected to said head section and extends axially outward from said circular end surface of said head section.

26. The fastener of claim 25, wherein said first recess includes a first opening which faces away from said external thread convolution and through which a first portion of a tool is movable to enable the first portion of the tool to apply force against surfaces of said first recess, said second recess includes a second opening which is separate from the first opening and faces away from said external thread convolution, a second portion of the tool being movable through the second opening to enable the second portion of the tool to apply force against surfaces of said second recess.

27. The fastener of claim 25, wherein the first recess includes a first opening which is at least partially disposed in said circular side surface of said head section and faces radially outward of said circular side surface of said head section and through which a first portion of a tool is movable to enable the first portion of the tool to apply force against surfaces of said first recess, said second recess having a second opening which is at least partially disposed in said circular side surface of said head section and faces radially outward of said circular side surface of said head section, a second portion of the tool being movable through the second opening to enable the second portion of the tool to apply force against surfaces of said second recess.

28. The fastener of claim 25, wherein the first recess includes a first opening which is at least partially disposed in said circular end surface of said head section and faces axially outward of said circular end surface of said head section in a direction away from said external thread convolution and through which a first portion of a tool is movable to enable the first portion of the tool to apply force against surfaces of said first recess, said second recess having a second opening which is at least partially disposed in said circular end surface of said head section and faces in a direction away from said external thread convolution, a second portion of the tool being movable through the second opening to enable the second portion of the tool to apply force against surfaces of said second recess.

29. The fastener of claim 25 wherein said first recess includes a first opening having a first portion which is disposed in said circular side surface of said head section and faces radially outward of said circular side surface of said head section and a second portion which is at least partially disposed in said circular end surface of said head section and faces axially outward of said circular end surface of said head section in a direction away from said external thread convolution, a first portion of a tool being movable through said first and second portions of the first opening to enable the first portion of the tool to apply force against surfaces of said first recess, said second recess having a second opening which is spaced from said first opening, said second opening having a first portion which is disposed in said circular side surface of said head section and faces radially outward of said circular side surface of said head section and a second portion which is at least partially disposed in said circular end surface of said head section and faces axially outward of said circular end surface of said head section in a direction away from said external thread convolution, a second portion of the tool being movable through said first and second portions of the second opening to enable the second portion of the tool to apply force against surfaces of said recess.

30. The fastener of claim 25, wherein the retaining section includes external thread means disposed on said retaining section for engaging an internally threaded retaining member.

31. An apparatus comprising a fastener, and tool means for applying force to said fastener to rotate said fastener relative to a vertebra, said fastener includes a mounting section have thread means for engaging the vertebra, said thread means includes an external thread convolution having flank surface means for engaging bone in the vertebra to hold said external thread convolution against axial movement relative to the vertebra, and a head section which is connected with said mounting section and projects radially outward of said external thread convolution, said head section includes a first recess means for receiving a first portion of said tool means, and a second recess means for receiving a second portion of said tool means, said second recess means is spaced from said first recess means, said first recess means includes a first opening having a first portion which faces outward of said head section in a direction away from a central axis of said fastener and a second portion which faces in a direction along the central axis of said fastener, said first portion of a tool means being moveable through said first and second portions of the first opening to enable said first portion of said tool means to apply force against surfaces of said first recess means to rotate said fastener, said second recess means having a second opening with a first portion which faces outward of said head section in a direction away from the central axis of said fastener and a second portion which faces in a direction along the central axis of the fastener, said second portion of the tool means being moveable through said first and second portions of said second opening to enable said second portion of said tool means to apply force against surfaces of said second recess means to rotate said fastener; and retainer means connected to said head section and extending away from said head section along the central axis of the fastener.

\* \* \* \* \*